United States Patent [19]

Moore

[11] Patent Number: 5,533,836
[45] Date of Patent: Jul. 9, 1996

[54] COMPOSITIONS AND METHODS FOR STIMULATING THE GROWTH OF OSTEOBLASTS

[75] Inventor: Emma E. Moore, Seattle, Wash.

[73] Assignee: ZymoGenetics, Inc., Seattle, Wash.

[21] Appl. No.: 408,331

[22] Filed: Mar. 22, 1995

Related U.S. Application Data

[63] Continuation of Ser. No. 38,325, Mar. 29, 1993, abandoned.

[51] Int. Cl.$^6$ .................................. C12N 5/02; C12N 5/08
[52] U.S. Cl. ........................ 435/240.31; 435/240.2; 435/240.25; 435/240.26; 514/12; 514/878
[58] Field of Search .................. 514/12, 878; 425/240.2, 425/240.25, 240.26

[56] References Cited

U.S. PATENT DOCUMENTS

| | | | |
|---|---|---|---|
| 4,264,512 | 4/1981 | Okamura et al. | 260/397.2 |
| 4,833,125 | 5/1989 | Neer et al. | 514/12 |
| 4,861,757 | 8/1989 | Antoniades et al. | 514/21 |
| 5,124,316 | 6/1992 | Antoniades et al. | 514/12 |
| 5,129,691 | 9/1992 | Rutherford | 514/12 |
| 5,254,538 | 10/1993 | Holick et al. | 514/35 |

FOREIGN PATENT DOCUMENTS

92/21365  12/1992  WIPO ............................ A61K 37/02

OTHER PUBLICATIONS

Watrous et al., *Semin. Arthritis Rheum.* USA 19:45–65, 1989.
Canalis et al., *Bone* 9:243–246, 1988.
Tsukamoto et al., *Biochem. Biophys. Res. Comm.* 175:745–751, 1991.
Abdennagy et al., *Cell Biology International Reports* 16:235–247, 1992.
Huffer, *Lab. Invest.* 59:418–442, 1988.
Dosquet–Bernard et al., *Cell Biology International Reports* 10:931–938, 1986.
Centrella et al., *Endocrinol.* 125:13–19, 1989.
Piche and Graves, *Bone* 10:131–138, 1989.
Lynch et al., *J. Peridontol.* 62:710–716, 1991.
Zhang et al., *Am. J. Physiol.* 261:C348–C354, 1991.
Suda et al., *J. Cell. Biochem.* 49:53–58, 1992.
Kurihara et al., *Endocrinol.* 118(3):940–947, 1986.
Lynch et al., *Proc. Natl. Acad. Sci.*, vol, 84, 7696–7700, 1987.
Webster's II New Riverside University Dictionary, Riverside Publishing Co. 1984, p. 1292.

*Primary Examiner*—Howard E. Schain
*Attorney, Agent, or Firm*—Deborah A. Sawislak

[57] ABSTRACT

Methods and compositions for stimulating the growth of osteoblasts are disclosed. A composition comprising platelet derived growth factor and vitamin D is applied to osteoblasts in an amount sufficient to stimulate their growth. The methods may be used to promote the growth of osteoblasts in vitro or to promote the healing of bone defects in vivo.

15 Claims, 7 Drawing Sheets

EFFECT OF OF 1α,25 DIHYDROXYCHOLECALCIFEROL AND PDGF BB ON PRIMARY PIG OSTEOBLASTS

PRETREATMENT VS. CONTINUOUS TREATMENT WITH
1α,25 DIHYDROXYCHOLECALCIFEROL

EFFECT OF 1α,25 DIHYDROXYCHOLECALCIFEROL

EFFECT OF 1α,25 DIHYDROXYCHOLECALCIFEROL ON bFGF ACTIVITY

EFFECT OF 1α,25 DIHYDROXYCHOLECALCIFEROL AND PDGF BB ON SWISS 3T3 CELLS

EFFECT OF 1α,25 DIHYDROXYCHOLECALCIFEROL AND PDGF BB ON MC3T3 CELLS

BONE RESORPTION INDUCED BY PDGF AND VITAMIN D

COMPOSITIONS AND METHODS FOR STIMULATING THE GROWTH OF OSTEOBLASTS

This is a continuation of U.S. patent application Ser. No. 08/038,325 filed Mar. 29, 1993, now abandoned.

BACKGROUND OF THE INVENTION

Bone remodeling is the dynamic process by which tissue mass and skeletal architecture are maintained. The process is a balance between bone resorption and bone formation, with two cell types thought to be the major players. These cells are the osteoclast and osteoblast. Osteoblasts synthesize and deposit new bone into cavities that are excavated by osteoclasts. The activities of osteoblasts and osteoclasts are regulated by many factors, systemic and local, including growth factors.

One of the growth factors believed to be involved in bone homeostasis is platelet-derived growth factor (PDGF). Biologically active PDGF is found as a homodimer or a heterodimer of the component A and B chains. In vitro studies have shown PDGF to be mitogenic for osteoblasts (Abdennagy et al. *Cell Biol. Internat. Rep.* 16(3):235–247, 1992). Mitogenic activity as well as chemotactic activities associated with PDGF have been demonstrated when the growth factor is added to normal osteoblast-like cells (Tuskamota et al. *Biochem. Biophys. Res. Comm.*, 175(3):745–747, 1991) and primary osteoblast cultures (Centrella et al. *Endocrinol.* 125 (1):13–19, 1989.). Recent studies have demonstrated that the osteoblast produces the AA isoform of PDGF (Zhang et al., *Am. J. Physiol.* 261:c348–354, 1991). The exact mode by which PDGF affects the growth of osteoblasts is not yet clearly understood, however, there does appear to be consensus that the growth factor plays a key role in the regulation of both normal skeletal remodeling and fracture repair.

The therapeutic applications for PDGF include, for example, the treatment of injuries which require the proliferation of osteoblasts to heal, such as fractures. Stimulation of mesenchymal cell proliferation and the synthesis of intramembraneous bone have been indicated as aspects of in fracture repair (Joyce et al. 36th Annual Meeting, Orthopaedic Research Society, Feb. 5–8, 1990. New Orleans, La.).

Vitamin D has traditionally been considered essential for the prevention of rickets, a disease of inadequate bone mineralization. This importance is associated with vitamin D's role in facilitating gastrointestinal uptake of calcium and the importance of serum calcium levels for bone homeostasis. Recent evidence suggests that osteoblasts have receptors for the vitamin D metabolite $1\alpha,25$-dihydroxycholecalciferol, indicating that the osteoblast is a major target for the hormone (Suda et al. *J. Cell. Biochem.*, 49:53–58, 1992). Vitamin D is believed to play an important part in activation by the osteoblast of osteoclast-mediated resorption (Watrous et al., *Sem. in Arthritis and Rheum.*, 19(1).:45–65, 1989). Vitamin D has been used in the in vitro culture of osteoblasts (Kurihara et al., *Endocrinol.* 118(3):940–947, 1986) and has been associated with an increase in alkaline phosphatase, a marker of cell differentiation into the osteoblastic phenotype. However, in human bone cells alkaline phosphatase stimulation has been associated with a decrease in cell proliferation (Huffer, *Lab. Investig.* 59(4):418–442, 1988). In calvarial cultures the addition of vitamin D increases the release of calcium into the medium and is correlated to bone resorptive activity (Bell, *J. Clinical Investig.* 76.:1–6, 1985). Expression of osteocalcin, a marker for osteoblasts, requires vitamin D induction (Yoon et al. *Biochem.* 27:8521–8526, 1988). The exact role of vitamin D in bone homeostasis and how it exerts its effects on the osteoblast and osteoclast remain to be elucidated.

Because of the important role of osteoblasts in the healing and regeneration processes of bone, an ability to enhance the proliferation of these cells remains a desirable objective. The present invention provides this ability and other advantages as will be apparent from the following detailed description and attached drawings.

SUMMARY OF THE INVENTION

The present invention is directed to methods of stimulating the growth of osteoblast cells by application of a composition that comprises platelet-derived growth factor (PDGF) and vitamin D. Within one embodiment, the composition is essentially free of PDGF A chain. Within a related embodiment, the composition comprises recombinant PDGF-BB. Within another embodiment, the cells are grown in vitro.

Another aspect of the present invention provides methods for stimulating bone growth in a patient by administering to the patient an effective amount of a composition that comprises PDGF and vitamin D. Within certain preferred embodiments the vitamin D is 9,10-secocholesta-5,7,10[19]-trien-3-ol or $1\alpha,25$-dihydroxycholecalciferol.

Within another aspect, the present invention provides methods for stimulating the growth of osteoblast cells by culturing the cells in the presence of an effective amount of a composition that comprises PDGF and vitamin D, wherein said composition is essentially free of the A-chain of PDGF.

These and other aspects of the invention will become evident upon reference to the following detailed description and the attached drawings.

DETAILED DESCRIPTION OF THE INVENTION

Figure 1:
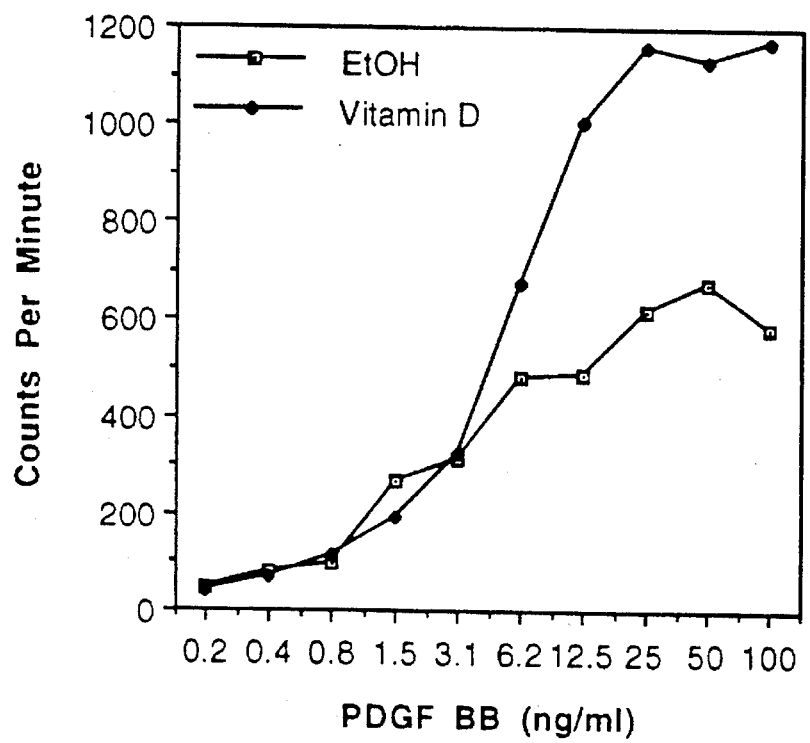
FIG. 1 illustrates that vitamin D increases the PDGF-BB stimulation of 3H-thymidine uptake in primary pig osteoblasts.

The present invention is based in part on the discovery by the inventors that PDGF and vitamin D exhibit a synergistic effect on the growth of osteoblasts. In addition, the inventors have found that PDGF can inhibit vitamin D-induced bone resorption. As noted above, osteoblasts play a central role in bone formation and bone homeostasis in general. The methods of the present invention are useful for stimulating growth of osteoblasts in in vitro cell cultures and in vivo (e.g. in repair of fractures), thereby promoting healing.

Within the context of the present invention, PDGF will be understood to include the AA, BB, and AB isoforms of PDGF, individually or in combination, as well as biologically active analogs thereof. In addition, the BB isoform of PDGF is understood to encompass its viral homolog (the v-sis gene product). PDGF may be obtained from either native or recombinant sources. Methods for producing recombinant PDGF and PDGF analogs are described within U.S. Pat. Nos. 4,769,322; 4,801,542; and 4,766,073 and within EP 282,317, which are incorporated herein by reference in their entirety. PDGF may also be produced in bacteria (see Tackney et al., WO 90/04035). Methods for purifying PDGF from native sources are described by Raines and Ross (*J. Biol. Chem.* 257: 5154– 5160, 1982), Hart et al. (*Biochemistry* 29: 166–172, 1990), and in U.S. Pat. No. 4,479,896.

As discussed in certain of the issued patents noted above, it has been found that by utilizing the secretory pathway of eucaryotic cells to express recombinant PDGF, biologically active material may be obtained directly. Expression and secretion of the appropriate gene product from eucaryotic cells enables proper processing and assembly, resulting in molecules with a native and biologically active conformation. Provided that appropriate transcriptional promoter and secretory signal sequences are utilized, generally any eucaryotic cell can express and secrete PDGF in a biologically active form for use within the present invention. In the alternative, PDGF polypeptide chains can be expressed in procaryotic cells, isolated, and assembled in vitro to produce biologically active molecules.

For expression of PDGF in yeast, a DNA sequence encoding a PDGF polypeptide (e.g. PDGF A chain or PDGF B chain) is ligated to an appropriate promoter and secretory signal sequence. Promoters which may be utilized in yeast include the yeast alpha-factor (MFα1) promoter and the yeast triose phosphate isomerase (TPI1) promoter (U.S. Pat. No. 4,559,311). Promoters may also be obtained from other yeast genes, e.g., alcohol dehydrogenase I (ADH1) or alcohol dehydrogenase 2 (ADH2). Appropriate promoters for other eucaryotic species may also be used and will be apparent to those skilled in the art. Secretion of the PDGF gene products may be accomplished through use of the prepro secretory signal sequence of the yeast mating pheromone alpha-factor (Kurjan and Herskowitz, *Cell* 30: 933, 1982; Julius et al., *Cell* 36: 309, 1984; and Brake et al., *Proc. Natl. Acad. Sci. USA* 81.: 4642, 1984), or the yeast BAR1 gene leader and third domain sequences (see U.S. Pat. No. 5,037,743), although other secretion signals may be used. To ensure the efficient transcription termination and polyadenylation of mRNA, a yeast terminator sequence, such as the triose phosphate isomerase terminator, may be added (Alber and Kawasaki, *J. Molec. Appl. Genet.* 1: 419, 1982). Methods of ligation of DNA fragments have been amply described (Sambrook et al., *Molecular Cloning: A Laboratory Manual,* 2nd Edition, Cold Spring Harbor Laboratory Press, 1989) and are well within the level of ordinary skill in the art. After preparation of the expression unit constructs, they are inserted into an appropriate expression vector.

It is preferable to use an expression vector which is stably maintained within the host cell in order to produce more biological activity per unit of culture. Suitable yeast expression vectors in this regard are the plasmids pCPOT (ATCC 39685) and pMPOT2 (ATCC 67788), which include the *Schizosaccharomyces pombe* gene encoding the glycolytic enzyme triose phosphate isomerase (POT1 gene). Inclusion of the POT1 gene ensures the stable maintenance of the plasmid in a host cell having a TPI gene deletion due to its ability to complement the gene deletion in the host cell, as disclosed in U.S. Pat. No. 4,931,373, which is incorporated herein by reference.

After preparation of a DNA construct incorporating the POT1 selectable marker and an expression unit comprising, for example, the TPI1 promoter, the BAR1 leader and third domain sequences, an appropriate DNA sequence encoding PDGF, and the TPI1 terminator, the construct is transformed into a yeast host with a TPI1 gene deletion. Procedures for transforming yeast are well known and have been described in the literature.

The transformed yeast cells may be selected by growth on a conventional complex medium containing glucose when the POT1 gene is utilized as a selectable marker. A conventional medium, such as YEPD (20 grams glucose, 20 grams Bacto-peptone, 10 grams yeast extract per liter), may be used. Once selected, transformants containing the appropriate expression constructs are grown to stationary phase on conventional complex media, the cells removed by centrifugation or filtration, and the medium concentrated. Since PDGF is a highly cationic and hydrophobic protein (Raines and Ross, *ibid.*; Antoniades, *Proc. Natl. Acad. Sci. USA* 78: 7314, 1981; Deuel et al. *J. Biol. Chem.* 256: 8896, 1981), recombinant PDGF similarly possesses characteristics which allow the use of ion exchange chromatography in its purification. For example, recombinant PDGF-BB in yeast fermentation broth is separated from the cells and fractionated by cation exchange chromatography. PDGF-BB desorbed from the column is acidified and further fractionated by reverse-phase chromatography under batch conditions. The PDGF-containing effluent is acidified and passed through a strong cation exchange column and eluted with a NaCl step gradient. The effluent is collected, and PDGF-BB is precipitated using $(NH_4)_2SO_4$. The resulting material is desalted by gel filtration and separated according to charge. The effluent is acidified and applied to a strong cation exchange column and eluted with a linear gradient of $NH_4HCO_3$ at pH 8–10. The effluent is collected, and the PDGF-BB is precipitated by the addition of $(NH_4)_2SO_4$. The resulting precipitate is dissolved in acetic acid and fractionated by gel filtration. The effluent is desalted and lyophilized.

Expression of biologically active proteins in eucaryotic cells other than yeast cells can be achieved by a person skilled in the art through use of appropriate expression/regulatory signals. Transcriptional promoters capable of directing the expression of PDGF sequences are chosen for their ability to give efficient and/or regulated expression in the particular eucaryotic cell type. Signal sequences capable of directing the gene product into the cell's secretory pathway are chosen for their function in the host cell. The selection of other useful regulatory signals, such as transcription termination signals, polyadenylation signals and transcriptional enhancer sequences, will be apparent to an individual skilled in the art.

Recombinant PDGF has been shown to possess substantially the same biological activity as native PDGF. The basic biological activity of PDGF, particularly the induction of chemotaxis and mitogenesis in responsive cell types (including fibroblasts, osteoblasts and smooth muscle cells), underlies many of the physiological roles of this protein, including its role in tissue repair.

Within preferred embodiments of the present invention the PDGF is essentially free of A chain. Because the homodimeric isoforms of PDGF (AA and BB) are homologous but not identical and monomers have molecular weights of 12.5–14.3 kD (A chain) and 13–14 kD (B chain), purity can be ascertained by the yield of a single, major band on a polyacrylamide gel.

PDGF compositions utilized within certain embodiments of the present invention are preferably substantially pure, that is, generally free of impurities or contaminants which would interfere with their therapeutic use. Particularly preferred are those preparations which are free of toxic, antigenic, inflammatory, pyrogenic or other deleterious substances, and are greater than 90%, preferably greater than 99%, pure.

As used herein vitamin D refers to both biologically active forms of the compound and precursors thereof that can be converted in vivo to a biologically active form. Vitamin D will therefore be understood to include, inter alia, vitamin $D_2$, vitamin $D_3$ and their active metabolites. Vitamin $D_2$ (9,10-Secoergosta-5,7,10[19], 22 -tetra-en-3-ol) is a synthetic form of vitamin D (Inhoffen, *Angew. Chem.* 72:875, 1960), and its biologically active metabolite is 25-hydroxy-ergocalciferol (Suda et al., *Biochem. Biophys. Res. Comm.* 25:182, 1969). Other metabolizable forms and analogs of these compounds may also be used, including 1-α-hydroxy vitamin $D_3$, 25-hydroxy vitamin $D_3$, 24,25-dihydroxy vitamin $D_3$, 1,25-dihydroxy vitamin $D_3$, 25-hydroxy vitamin $D_2$, 1,25-dihydroxy vitamin $D_2$, 24,25-dihydroxy vitamin $D_2$ and others known in the art. A preferred compound is vitamin $D_3$ (9,10-Secocholesta-5,7,10,[19]-trien-3-ol), and most preferred is the biologically active form of the compound, 1α, 25-dihydroxycholecalciferol, both of which are commercially available.

Within one embodiment the present invention serves to stimulate the growth of osteoblasts in vitro. It is often the case that osteoblasts are derived from a primary culture, that is a culture obtained directly from a tissue containing a heterogeneous population of cell types. Primary cultures from bone tissue may contain osteoclasts, fibroblasts, osteoblast progenitor cells and endothelial cells. Primary cultures may be established using several methods well known in the art. For example, fetal calvaria that is ground and incubated in the presence of collagenase may be used to establish a primary culture. Cells released by collagenase digestion are collected and cultured (Aubin et al., *J. of Cell Biol.*, 92:452–461, 1982). Alternative methods use freshly isolated bone chips that are collagenase treated and washed, then cultured to allow migration of cells from the bone chips and use of a low $Ca^{++}$ medium that selects for the growth of osteoblasts after collegenase treatment (Robey et al., *Calif. Tiss.* 37:453–460, 1985). Identification of osteoblasts within a primary culture is primarily phenotypic. The phenotypic markers for osteoblasts include expression of alkaline phosphatase (Manduca et al., *J. Bone Min. Res.* 8: 281, 1993), type 1 collagen synthesis (Kurihara et al., *Endocrinol.* 118(3):940–947, 1986), production of osteocalcin (Yoon et al., ibid.) and responsiveness to parathyroid hormone (Aubin et al., ibid.). Osteoblast cells are typically cultured at 37° C. in 5% $CO_2$ in a growth medium that includes a carbon source, a nitrogen source, essential amino acids, vitamins, minerals and growth factors generally supplied by fetal calf serum. A variety of suitable media are known in the art.

The present invention may also be used to stimulate the growth of established osteoblast cell lines. Examples of such cell lines include: Saos-2, a human primary osteogenic sarcoma (ATCC No. HTB 85); U-2 OS, a human primary osteogenic sarcoma (ATCC No. HTB 964); HOS (TE85), a human osteogenic sarcoma (ATCC No. CRL 1543); MG-63, a human osteosarcoma (ATCC No. CRL 1427) and UMR 106, a rat osteosarcoma (ATCC No. CRL 1661).

In another embodiment of the present invention, a composition comprising PDGF and vitamin D is used as a therapeutic to enhance osteoblast-mediated bone formation. The methods of the invention may be applied to promote the repair of bone defects and deficiencies, such as those occurring in closed, open and non-union fractures; to promote bone healing in plastic surgery; to stimulate bone ingrowth into non-cemented prosthetic joints and dental implants; in the treatment of peridontal disease and defects; to increase bone formation during distraction osteogenesis; and in treatment of other skeletal disorders that may be treated by stimulation of osteoblastic activity, such as osteoporosis and arthritis.

The compositions of the present invention may be administered locally or systemically. Local administration may be by injection at the site of injury or defect or by insertion or attachment of a solid carrier at the site, or by direct, topical application of a viscous liquid.

Delivery of biologically active PDGF and vitamin D to wound sites may be enhanced by the use of controlled-release compositions such as those described in pending U.S. patent application Ser. No. 07/871,246 which is incorporated herein by reference in its entirety. Briefly, biodegradable polyester films, such as polylactic acid, polyglycolic acid, polydioxanone or polylactic acid/polyglycolic acid copolymer films, containing PDGF are prepared and fabricated into pins, plates, screws and the like for attachment to or insertion into bone. These compositions provide for the sustained release of PDGF at the target site. 50:50 PLA:PGA films are preferred. These films may further include a carrier such as albumin, a polyoxyethylenesorbitan detergent or glutamic acid. When albumin is included, the ratio of PDGF to albumin will, in general, be maintained between 0.125 and 2.5 µg/mg. In principle, any substance that enhances polymer degradation, creates pores in the film or reduces adsorption of the growth factor(s) to the film can be used as a carrier. Albumin is a particularly preferred carrier. Polyoxyethylenesorbitan detergents that are useful as carriers include polyoxyethylenesorbitan monooleate, polyoxyethylenesorbitan monolaureate, polyoxyethylenesorbitan monopalmitate, polyoxyethylenesorbitan monostearate and polyoxyethylenesorbitan trioleate.

Films of this type are particularly useful as coatings for prosthetic devices and surgical implants. The films may, for example, be wrapped around the outer surfaces of surgical screws, rods, pins, plates and the like. Implantable devices of this type are routinely used in orthopedic surgery. The films can also be used to coat bone filling materials, such as hydroxyapatite blocks, demineralized bone matrix plugs, collagen matrices and the like. In general, a film or device as described herein is applied to the bone at the fracture site. Application is generally by implantation into the bone or attachment to the surface using standard surgical procedures.

In addition to the copolymers, growth factors and carriers noted above, the biodegradable films may include other active or inert components. Of particular interest are those agents that promote tissue growth or infiltration. Agents that promote bone growth, such as bone morphogenic proteins (U.S. Pat. No. 4,761,471; PCT Publication WO 90/11366), osteogenin (Sampath et al., *Proc. Natl. Acad. Sci. USA* 84: 7109–7113, 1987) and NaF (Tencer et al., *J. Biomed. Mat. Res.* 23: 571–589, 1989) are particularly preferred.

To load the films, PDGF and a carrier are applied to the film as powders or liquid solutions. For example, lyophilized PDGF and albumin may be uniformly dispersed over one surface of the film, and the film folded over. In the alternative, the proteins may be applied as aqueous solutions (e.g., in phosphate buffered saline or 0.1M acetic acid), which are allowed to dry.

Biodegradable materials containing PDGF may also be molded into a variety of implants according to procedures known in the art. Pins, plates, blocks, screws and the like can be fabricated for insertion into or attachment to bone at the site of a fracture or other defect.

Biodegradable materials are typically formulated to contain between 0.0375 and 1.25 µg of PDGF per mg of copolymer.

Alternative methods for local delivery of PDGF and/or vitamin D include use of ALZET osmotic minipumps (Alza Corp. Palo Alto, Calif.); sustained release matrix materials such as those disclosed in Wang et al. (WO 90/11366); electrically charged dextran beads as disclosed in Bao et al. (WO 92/03125); collagen-based delivery systems, for example, as disclosed in Ksander et al. (*Ann. Surg.* 211(3):288–294, 1990); methylcellulose gel systems as disclosed in Beck et al. (*J. Bone Min. Res.* 6(11):1257– 1265, 1991) and alginate-based systems as disclosed in Edelman et al. (*Biomaterials,* 12:619–626, 1991). Other methods well known in the art for sustained local delivery in bone include porous coated metal protheses that can be impregnated and solid plastic rods with therapeutic compositions incorporated within them.

Delivery of systemically adminstered compositions of the present invention may be enhanced by conjugating one or both of PDGF and vitamin D to a targeting molecule. "Targeting molecule" refers to a molecule that binds to the tissue of interest. For example, bone-targeting molecules include tetracyclines; calcein; bisphosphonates; polyaspartic acid; polyglutamic acid; aminophosphosugars; peptides known to be associated with the mineral phase of bone such as osteonectin, bone sialoprotein and osteopontin; bone specific antibodies; proteins with bone mineral binding domains and the like. See, for example, the disclosures of Bentz et al. (EP 0512844) and Murakami et al. (EP 0341961).

Compositions used within the present invention may be in the form of pharmaceutically acceptable salts, especially acid-addition salts including salts of organic acids and mineral acids. Examples of such salts include organic acids such as formic acid, acetic acid, propionic acid, glycolic acid, lactic acid, pyruvic acid, oxalic acid, succinic acid, malic acid, tartaric acid, citric acid, benzoic acid, salicylic acid and the like. The acid-addition salts of the basic amino acid residues are prepared by treatment of the peptide with the appropriate acid or mineral according to procedures well known to those skilled in the art, or the desired salt may be obtained directly by lyophilization out of the appropriate acid. These salts may further be used in the preparation of injectables, topicals and aqueous solutions for local or systemic delivery of compositions of the present invention. Materials and methods for manufacturing injectables and topicals can be found in *Remington's Pharmaceutical Sciences,* 17ed., 1985, and is incorporated herein by reference it its entirety.

Within the present invention, an "effective amount" of a composition is that amount which produces a statistically significant effect. When used to stimulate the growth of osteoblast cells in vitro, it is generally desirable to produce an increase in growth of at least 50%, as measured by incorporation of $^3$H-thymidine, as compared to cells grown in the presence of PDGF and absence of vitamin D. For therapeutic uses, an "effective amount" is the amount of the composition comprising PDGF and vitamin D required to provide a clinically significant increase in healing rates in fracture repair, reversal of bone loss in osteoporosis, stimulation and/or augmentation of bone formation in fracture non-unions and distraction osteogenesis, increase and/or acceleration of bone growth into prosthetic devices and repair of dental defects. Such amounts will depend, in part, on the particular condition to be treated and other factors evident to those skilled in the art. For example in osteoporosis, increase in bone formation is manifested as a statistically significant difference in bone mass between treatment and control groups. This can be seen as, for example, a 10–20% or more increase in bone mass. Other measurements of clinically significant increases in healing may include, for example, tests for breaking strength and tension, breaking strength and torsion, 4-point bending and other biomechanical tests well known to those skilled in the art. General guidance for treatment regimens is obtained from experiments carried out in animal models of the disease of interest.

A preferred dose range for vitamin D for systemic treatment of a 70-kg patient is from about 1 ng to 1 mg, preferably from about 10 ng to about 500 µg, and most preferably from about 20 ng to 1 µg. A preferred dose range for vitamin D for local application of vitamin D in combination with PDGF is from about 1 ng to 1 mg, preferably from about 5 ng to about 500 ng, and most preferably from about 10 ng to 100 ng.

A preferred dose range for administration of PDGF for systemic treatment of a 70 kg patient is from about 1 pg to about 10 mg, preferably from 100 pg to 1 mg and most preferably from 10 ng to 100 µg. A preferred dose range for local application of PDGF in combination with vitamin D is from about 1 ng to about 10 mg, preferably from 1 µg to 1 mg and most preferably from 10 µg to 500 µg. In general, sustained release compositions will be formulated to provide doses in the higher ends of the stated ranges. Doses will be adjusted to the release rate. Liquid formulations will typically contain from 1– 1000 µg/ml of PDGF, preferably 10–500 µg/ml.

In vitro, the preferred range for PDGF concentration is about 1 ng/ml to 100 ng/ml, preferably 5 ng/ml to 40 ng/ml and most preferably 6 ng/ml to 20 ng/ml.

It has been found that the synergistic effect of PDGF and vitamin D is best obtained by combining the PDGF and vitamin D in a ratio of from 6:0.1 to 6:1000 (PDGF: vitamin D), preferably 6:1 to 6:500, more preferably 6:10 to 6:100, most preferably about 6:40.

The compositions described above are administered over a period ranging from a day to 6 months or more, depending on the condition to be treated. In general, doses will be adminstered from 5 times a day to once a month and preferably from once a day to once a month until healing is substantially complete. The actual treatment regimen will depend upon such factors as the age and general condition of the patient, the condition to be treated, and the route of delivery. Determination of treatment regimen is within the level of ordinary skill in the art.

The invention is illustrated by the following non-limiting examples.

EXAMPLE I

A pig primary osteoblast culture was established. The trabecular bone portions were removed from the femurs of an immature pig (approximately 30 lbs). The bone was cut into small chips, approximately 2×2 mm, and washed multiple times at room temperature in phosphate buffered saline (PBS) to remove all blood. The bone chips were placed in 1 mg/ml *Clostridium histolyticum* Type II collagenase (Sigma Chemical Co., St. Louis, Mo.) that had been diluted in Dulbecco's medium (DMEM) (Fred Hutchinson Cancer Research Center, Seattle, Wash.) and filter sterilized before use. The chips were incubated in the collagenase medium for 2 hours at 37° C. while shaking. After the collagenase incubation the medium was removed, and the bone chips were placed in PBS and washed until no more cells were present in the wash medium.

The chips were placed in Eagles-MEM medium (GIBCO-BRL, Gaithersburg, Md.) containing 10% fetal calf serum (FCS) (Hyclone, Logan, Utah), 1 mM sodium pyruvate and 0.29 mg/ml L-glutamine at a low density and incubated at 37° C. and 5% $CO_2$. The medium was changed every 4–5 days. Osteoblast migration from the bone chips was seen in 7–10 days. The cells were used immediately for assay once confluent and then discarded.

The cells were tested for expression of alkaline phosphatase to confirm osteoblastic phenotype. Histochemical staining was performed using AP Histochemical Staining kit 86R (Sigma, St. Louis, Mo.), according to the manufacturer's specifications. Results indicated 30–70% of the heterogeneous primary cell population were alkaline phosphatase positive and increasing cell density increased the percentage of AP+ cells.

EXAMPLE II

Pig primary osteoblasts (prepared as described above) were tested for relative mitogenic activity in the presence of PDGF-BB, PDGF-BB and 1α,25-dihydroxycholecalciferol, and 1α,25-dihydroxycholecalciferol alone. Mitogenic activity was assayed by measurement of $^3$H-thymidine incorporation based on the method of Raines and Ross (*Meth. Enzymology* 109:749–773, 1985). Briefly, quiescent primary pig osteoblasts were obtained by plating cells at a density of $3 \times 10^4$ cells/ml in Eagles MEM medium (GIBCO-BRL, Gaithersburg, Md.) containing 10% fetal calf serum (FCS) in 96-well plates and allowing them to grow for 3–4 days. The medium was removed, and 180 μl of DFC (Table 1) containing 0.1% FCS was added per well. Half the wells had 10 nM 1α,25-dihydroxycholecalciferol (Biomol. Research Labs, Plymouth Meeting, Pa.) added to them. The cells were incubated for 3 days at 37° C. in 5% $CO_2$. Because 1α,25dihydroxycholecalciferol was dissolved in ethanol, another set of wells were prepared as a control containing an equivalent amount of ethanol as that which was introduced by the addition of the 1α,25-dihydroxycholecalciferol. Twenty microliters of 10× PDGF was added so that the final concentration ranged from 0.2–50 ng/ml. Negative controls were set up without PDGF-BB added and +/− the vitamin D addition. The plates were incubated 20 hours at 37° C. and the medium was removed. One hundred microliters of DFC containing 0.1% FCS and 2 μCi/ml $^3$H-thymidine was added to each well, and the plates were incubated an additional 3 hours at 37° C. The medium was aspirated off, and 150 μl of trypsin was added to each well. The plates were incubated at 37° C. until the cells detached (at least 10 minutes). The detached cells were harvested onto filters using an LKB Wallac 1295-001 Cell Harvester (LKB Wallac, Pharmacia, Gaithersburg, Md.). The filters were dried by heating in a microwave oven for 10 minutes and counted in an LKB Betaplate 1250 scintillation counter (LKB Wallac) as described by the supplier.

TABLE 1

250 ml Dulbecco's Modified Eagle's Medium (DMEM)
250 ml Ham's F12 medium
0.29 mg/ml L-glutamine
1 mM sodium pyruvate
25 mM Hepes (Sigma, St. Louis, Mo.)
10 μg/ml fetuin (Aldrich, Milwaukee, Wis.)
50 μg/ml insulin (GIBCO-BRL)
3 ng/ml selenium (Aldrich, Milwaukee, Wis.)
20 μg/ml transferrin (JRH, Lenexa, Kans.)

The results, as illustrated in FIG. 1, show that PDGF-BB stimulates thymidine uptake in the primary pig osteoblast cultures. Maximal stimulation occurs at 6–10 ng/ml. Including 10 nM 1α,25-dihydroxycholecalciferol with the PDGF doubles the maximal uptake of thymidine. No growth stimulation was observed in the presence of 1α,25-dihydroxycholecalciferol alone.

EXAMPLE III

To determine whether 1α,25-dihydroxycholecalciferol and PDGF must be present simultaneously for the synergistic growth effect to be observed, the mitogenic assay was performed as described in Example II with the following modifications: a) the final concentration of the 1α,25-dihydroxycholecalciferol was 100 nM; b) an additional set of wells were prepared without 1α,25-dihydroxycholecalciferol in the presence of PDGF by removing the medium used to pretreat the cells with 1α,25-dihydroxycholecalciferol and adding fresh medium containing only the appropriate dilutions of PDGF.

Figure 2:
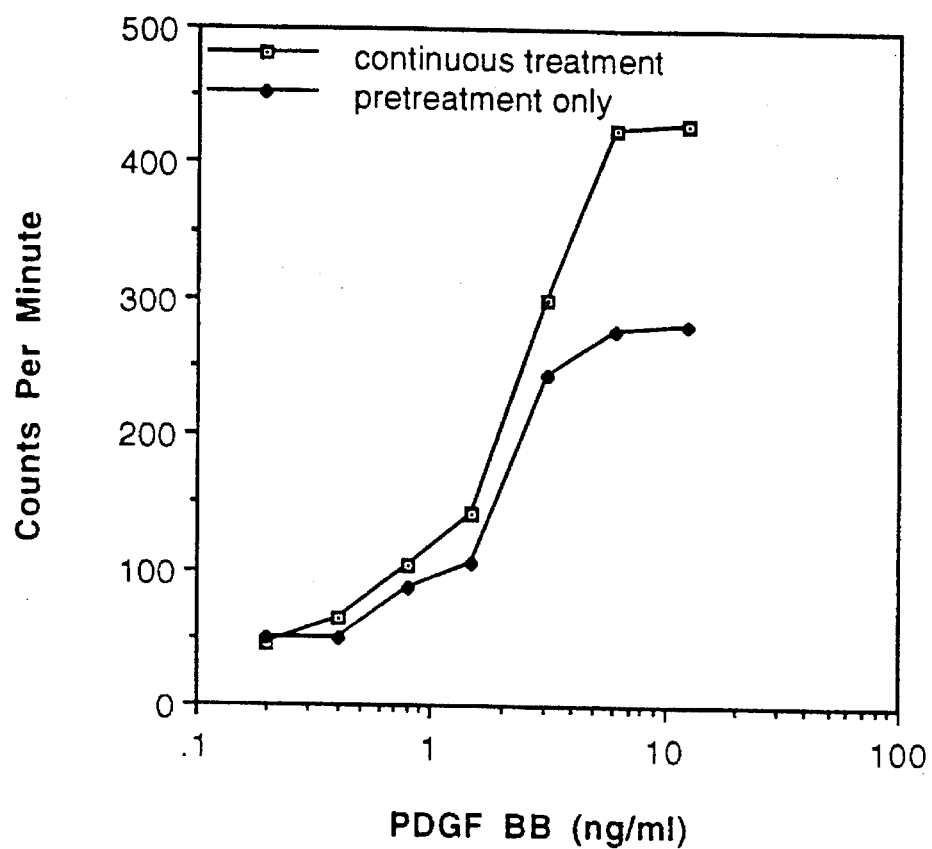
FIG. 2 illustrates that both PDGF and vitamin D must be present simultaneously to observe the two-fold increase in mitogenesis.

The results, as illustrated in FIG. 2, demonstrate that both PDGF and 1α,25-dihydroxycholecalciferol must be present simultaneously to observe the 2-fold increase in mitogenesis.

EXAMPLE IV

Figure 3:
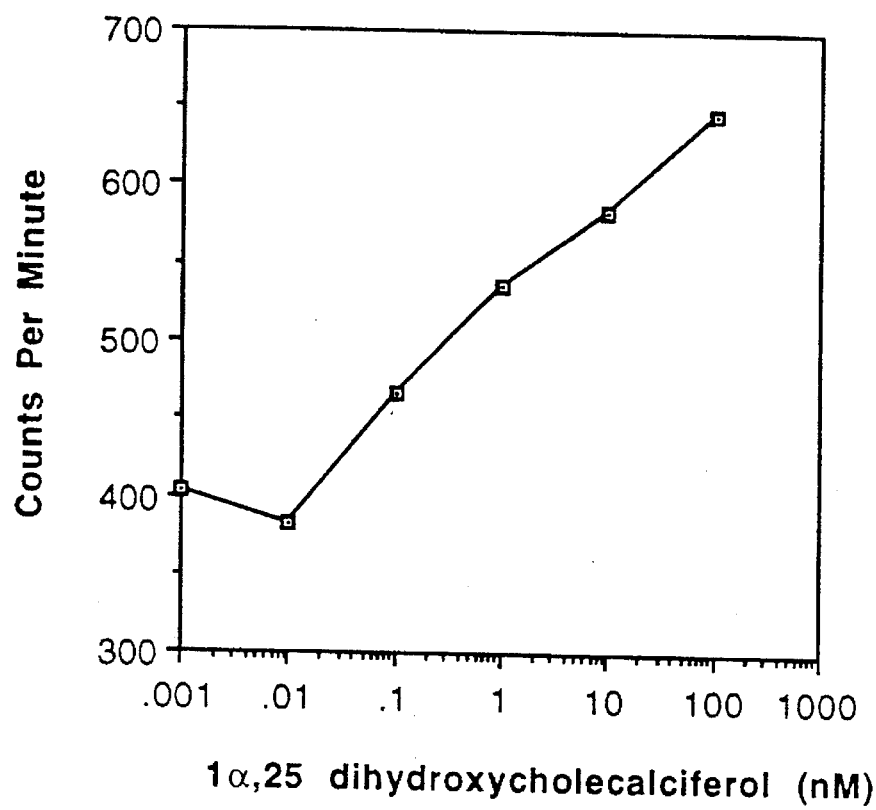
FIG. 3 illustrates that the synergistic effect of PDGF and vitamin D varies with the concentration of vitamin D.

To determine whether the effect of 1α,25-dihydroxycholecalciferol on PDGF-induced mitogenesis on primary pig osteoblasts is dose dependent, an assay was performed as described in Example II with the following modifications: a) the concentration of 1α,25-dihydroxycholecalciferol ranged from 0.01 nM to 100 nM and b) PDGF was present at a single concentration of 6.2 ng/ml. The results, as illustrated in FIG. 3, demonstrate that the synergistic effect of PDGF and 1α,25-dihydroxycholecalciferol varies with the concentration of 1α,25-dihydroxycholecalciferol.

EXAMPLE V

Figure 4:
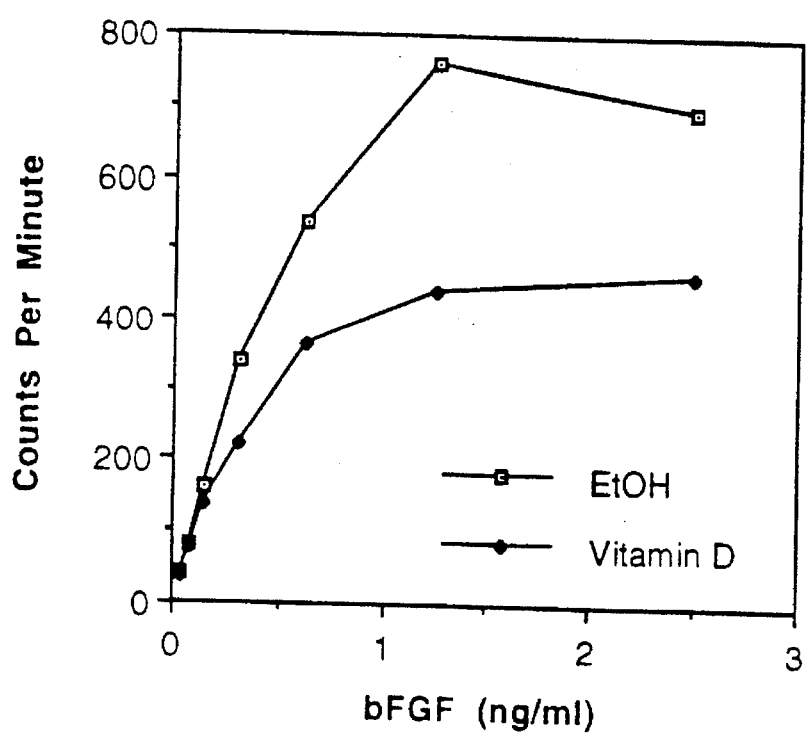
FIG. 4 illustrates that the synergistic effect is not present when basic FGF and vitamin D is used.

To determine if the effects seen with vitamin D are specific for PDGF, vitamin D was tested in combination with basic fibroblast growth factor (FGF). Human recombinant basic FGF (BRL-GIBCO) was tested at concentrations ranging from 0.4 ng/ml to 100 ng/ml in the mitogenic assay described in Example II. The results, shown in FIG. 4, show the effect is not present when basic FGF and 1α,25-dihydroxycholecalciferol are used.

EXAMPLE VI

Figure 5:
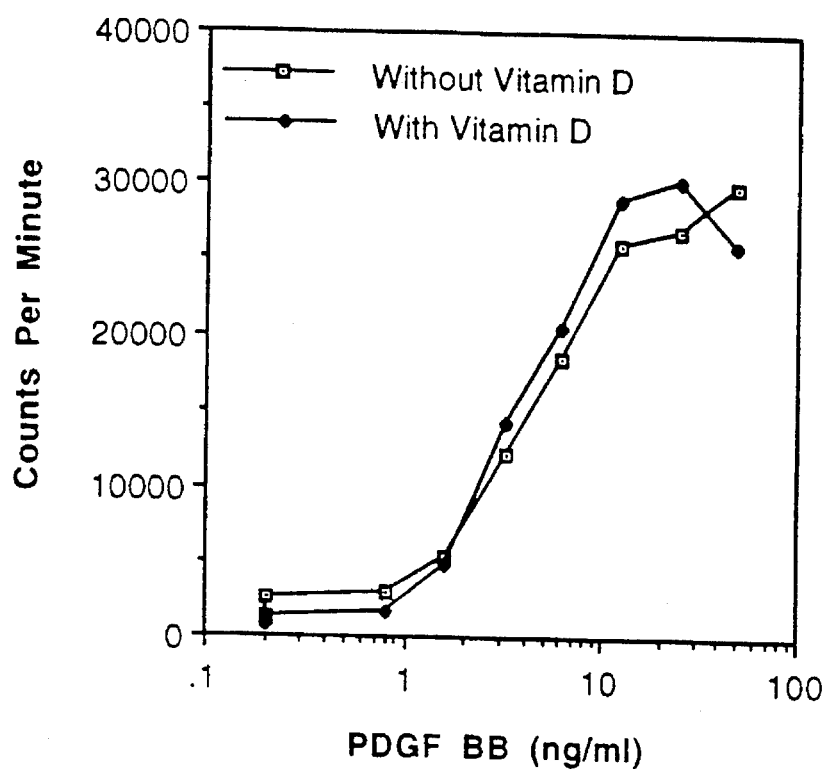
FIG. 5 illustrates that vitamin D does affect the PDGF-induced mitogenesis of Swiss 3T3 fibroblasts.

An assay was performed to determine if in fibroblasts, a potential contaminating cell type primary cultures from bone, were responsible for the synergistic effect seen with PDGF and 1α,25-dihydroxycholecalciferol. Using the mouse fibroblast cell line Swiss 3T3 (ATCC No. CCL92) the assay was performed as described in Example II with the exception that the fibroblast cells were plated in DMEM containing 10% FCS at a density of $3 \times 10^4$ cells/ml. The results, shown in FIG. 5, demonstrate that 1α,25-dihydroxycholecalciferol does not affect the PDGF-induced mitogenesis of these fibroblast cells.

EXAMPLE VII

Figure 6:
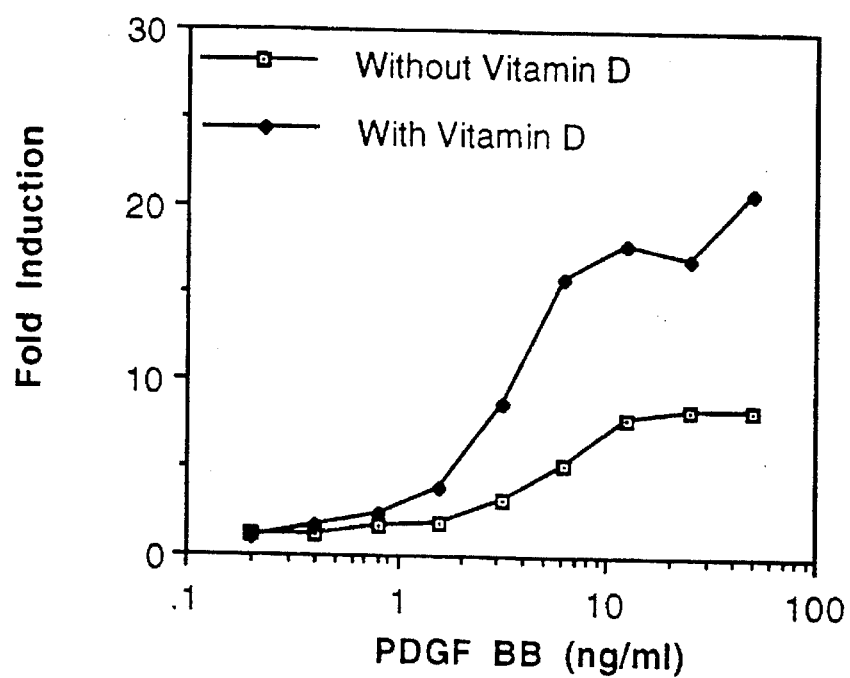
FIG. 6 illustrates that PDGF induces a greater fold-induction in the presence of vitamin D than in the absence of vitamin D for a mouse osteblast cell line, MC3T3.

To verify that the synergistic effect of 1α,25-dihydroxycholecalciferol and PDGF is seen in osteoblasts, an established osteoblast mouse cell line, MC3T3 (Suda et al., *J. Cell Biol.* 96:191–198, 1983) was used. The assay was performed essentially as described in Example II with the exception that the cells were plated at a density of $3 \times 10^4$ cells/ml in α-MEM medium (GIBCO-BRL) with 10% FCS. In contrast to both the Swiss 3T3 fibroblasts and the primary pig osteoblasts, 1α,25-dihydroxycholecalciferol inhibited the growth of the MC3T3 cells. Therefore, the data were analyzed in terms of the fold-induction of thymidine uptake. Fold induction is defined as the ratio of cpm of $^3$H-thymidine incorporated in the presence of PDGF to those obtained in the absence of PDGF. The results, as illustrated in FIG. 6, show that PDGF induces a greater fold-induction in the presence of 1α,25-dihydroxycholecalciferol than in the absence of the vitamin.

EXAMPLE VIII

To verify that osteoblasts in the pig primary bone cultures were responding to PDGF and 1α,25-dihydroxycholecalciferol, assays were carried out for mitogenesis and alkaline phosphatase expression. Pig primary bone cells were assayed for $^3$H-thymidine uptake and expression of the osteoblast marker alkaline phosphatase within the same cells. The pig primary bone cells were plated and treated as described above with the following exceptions: a) the cells were plated in Lab-tek chamber slides No. 177445 (All World Scientific, Seattle, Wash.); b) a single concentration of 100 ng/ml PDGF-BB was used; and c) a single concentration of 10 nM 1α,25-dihydroxycholecalciferol was used. After incorporation of $^3$H-thymidine, the slides were washed three times with PBS and stained for alkaline phosphatase expression as described previously. After staining, the slides were air dried and coated with NTB3 emulsion (Kodak, Rochester, N.Y.). The emulsion was allowed to air dry, and the slides were placed at 4° C. and exposed for one week. After exposure the slides were developed 5 minutes in D-19 developer (Kodak) at room temperature, rinsed in water and fixed in Rapid Fixer (Kodak) for 5 minutes. The slides were counterstained with methylene blue (Sigma) by diluting the stock 1:100 in water and applying to cells for one minute.

The cells expressing alkaline phosphatase (AP+) were identified by their pink color, whereas cells having incorporated $^3$H-thymidine were identified by the accumulation of silver grains over their nuclei. In the absence of PDGF-BB only 2–4% of the cells incorporated $^3$H-thymidine, and this percentage was not affected by the addition of 1α,25-dihydroxycholecalciferol. Addition of PDGF-BB increased the percentage of cells which had incorporated $^3$H-thymidine by approximately ten-fold. Both AP+ and AP– cells were responsive to PDGF-BB. The percentage of AP+ cells which had incorporated $^3$H-thymidine in response to PDGF in the presence or absence of 1α,25-dihydroxycholecalciferol was calculated. Similar calculations were made for AP– cells. The results are summarized in Table 2. The addition of 1α,25-dihydroxycholecalciferol increased the number of AP+ cells that had incorporated thymidine by almost two-fold, whereas a more modest increase was observed for the AP– cells. These results demonstrate that the osteoblasts in the culture, as identified by their expression of AP, show a synergistic response to 1α,25-dihydroxycholecalciferol and PDGF-BB. The identity of the AP– cells that show a synergistic response to 1α,25-dihydroxycholecalciferol and PDGF-BB may or may not be osteoblasts, as osteoblasts do not express AP at all stages of their differentiation.

TABLE 2

| | cells incorporating $^3$H-thymidine | |
|---|---|---|
| cell population | without vitamin D | with vitamin D |
| alkaline phosphatase positive | 31% | 55% |
| alkaline phosphatase negative | 41% | 54% |

EXAMPLE IX

Vitamin D is known to be a potent stimulator of bone resorption when added to an in vitro calvarial assay, and PDGF has been shown to have modest bone resorptive effect in this assay. Because bone resorption is a contraindication for stimulation of bone formation, evaluation of the interaction of PDGF and vitamin D in a bone resorption assay was made.

Calvaria, which included parietal bone with the sagital suture, were collected from 4-day old CD-1 mice (Charles River Laboratories, San Diego, Calif.). The bones were placed in 6 well petri dishes (American Science Products, McGraw Park, Ill.) with 1 ml of growth medium (DMEM, 0.29 mg/ml L-glutamine, 1 mM sodium pyruvate, and 15% heat inactivated horse serum (HIHS)) and incubated at 37° C. in 5% $CO_2$ shaking gently for 24 hours. After the incubation, the medium was removed from the wells and replaced with 1.5 ml growth medium containing either 200 ng/ml PDGF-BB, $10^{-8}$M 1α,25-dihydroxycholecalciferol, or both PDGF and vitamin D. Five bones were in each sample group, and the groups were incubated rocking at 37° C., 5% $CO_2$ for 72 hours. After the incubation, the medium was removed from the wells and analyzed for $Ca^{++}$ levels using a NOVA-7 total calcium analyzer (Nova Biomedical, Waltham, Md.) according the manufacturer's specifications. In addition to the sample media, medium from the 24 hour incubation was analyzed to ensure that none of the bones had been damaged during the collection process. Damaged bones release high levels of calcium into the medium and were not used in the final analyses.

Figure 7:
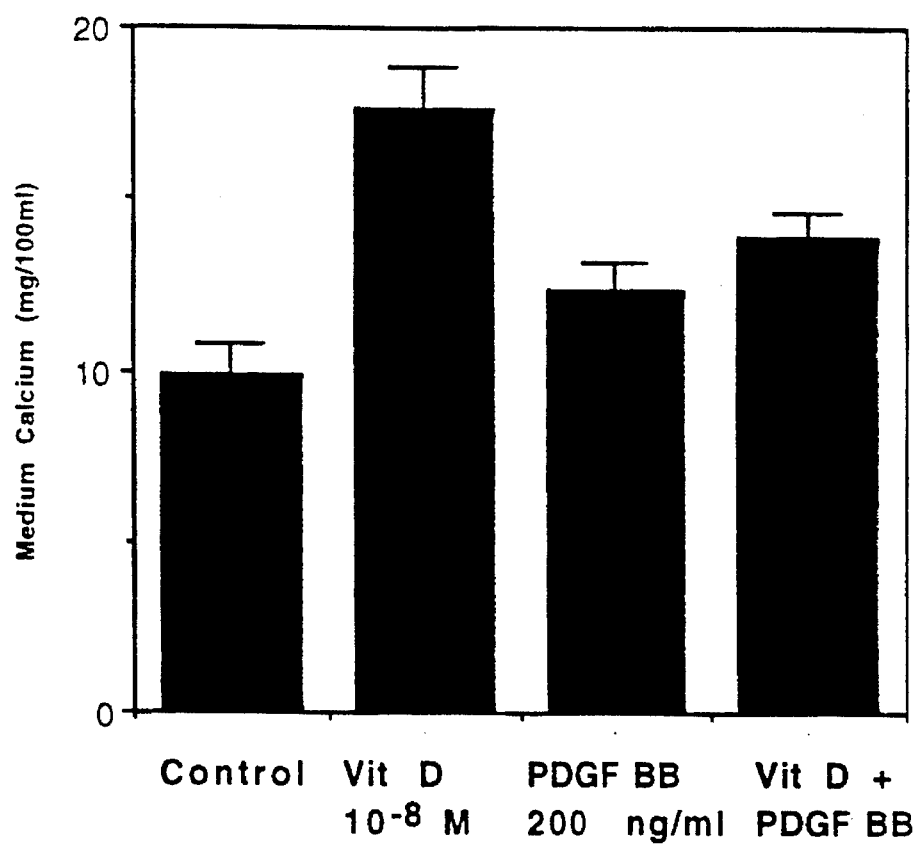
FIG. 7 illustrates that PDGF and vitamin D stimulate bone resorption when added to separate calvarial cultures but that PDGF and vitamin D added together to a calvarial culture demonstrate a reduction in bone resorption.

The results, shown in FIG. 7, show that both PDGF and 1α,25-dihydroxycholecalciferol stimulated bone resorption when added to calvaria separately. However, when PDGF and 1α,25-dihydroxycholecalciferol were added in combination, the levels of $Ca^{++}$ release due to bone resorption seen with vitamin D were reduced, indicating an inhibitory effect of PDGF.

EXAMPLE X

To test the ability of PDGF and vitamin D to synergistically increase bone ingrowth into a porous hydroxyapatite implant, cylindrical implants of 25 mm in length and 4 mm in nominal diameter are machined from (Interpore, Irvine, Calif.) hydroxyapatite material of a pore size of 190–230 μm. The cylinders contain an undercut region, 10 mm and 3 mm in diameter. Implants are loaded with PDGF by immersing the implant in a solution of PDGF that results in doses of 0.5–50 ng/implant. The vitamin D is administered locally using an ALZET minipump (Alza Corp.) and results in doses of vitamin D of 10–100 ng/implant. The dose ratio of PDGF to vitamin D is 1:6. Vehicle loaded implants are used as controls.

Twenty-four skeletally mature New Zealand White rabbits with an average weight of 3.5 kg are used in the study. Anesthesia is performed by injection of 5.0 mg/kg of xylazine and 35.0 mg/kg of ketamine into each paraspinous muscle by half doses. The animals are then intubated, and anesthesia is maintained using halothane gas.

The intramedullary implants are inserted using a distal approach (Anderson et al., J. Orthop. Res. 10:588– 595, 1992). A 2.5 cm lateral parapatellar incision is made entering the knee along the lateral edge of the patellar tendon. The patella is dislocated medially with the leg in extension. A 4.0 mm drill bit is introduced between the femoral condyles, directly proximally. Once through the articular cartilage and metaphyseal bone, the hole is probed to confirm intramedullary positioning. The implant is inserted and pushed proximally to its final position. Bone wax is used to plug the distal entrance hole. The wound is closed in layers with 4-0 absorbable suture and stainless steel suture.

Analyses are histological and biomechanical. Cross-sectional sections are made to yield 3.5 mm long femoral bone specimens with implants such that the following regions can be studied: adjacent to the trabecular region of the proximal femur, at the gap site and adjacent to endosteal cortex of the midproximal part of the femur. For each site the specimen is bisected with one used for histology and the other for biomechanical studies. Each experimental site is compared to vehicle loaded controls from the contralateral femur.

Histological specimens are fixed in phosphate buffered formalin and dehydrated in an ascending series of alcohol (EtOH): 95% EtOH for 24 hours followed by three changes in 100% EtOH of 24 hours each. After the final 100% EtOH treatment the specimens are cleared in two changes of xylene for 24 hours each. Tissue infiltration for plastic embedding is carried out. Specimens are oriented for transverse sectioning in plastic rods and embedded in methacrylate plastic at room temperature in a vacuum desiccator under nitrogen atmosphere as disclosed in Bain et al. (*Stain Technol.* 65(4):159, 1990). From each sampling site 150 μm sections are prepared using a low-speed diamond wheel saw (Struers Accutom-2, Torrance, Calif.). Thick sections are then hand ground to approximately 30 μm between two glass slides covered with 1200 grit emery cloth. Ground sections are mounted on glass slides with Immuno-Mount (Shandon, Pittsburgh, Pa.).

The area properties for bone ingrowth into the implant and dynamic indices of bone formation are determined using the Bioquant bone morphometry program (Biometrics, Inc., Nashville, Tenn.) interfaced via a camera lucida with an Olympus BH-2 light/epifluorescent microscope (Scientific Instruments, Inc., Redmond, Wash.). Total bone ingrowth into the implant is measured under fluorescent microscopy at ×40 magnification. Parameters of mineral apposition and bone formation are determined from in vivo fluorochrome labels at ×100 magnification. The mean interlabel widths at the implant interface are divided by the interlabel time period to calculate mineral apposition rates. Total bone formation rates, are determined by tracing the area of newly formed bone (i.e., the bone bounded by fluorochrome labels) and dividing the total new bone area by the interlabel time.

Bone ingrowth is evaluated mechanically using a pushout test. Specimens to be tested are mounted on an Instron testing apparatus and a constant force is applied at 0.5 mm/sec to the center of the implant. The force required to push out the implants is determined using biomechanical testing procedures well known to those skilled in the art, as disclosed in Knowles et al. (*Biomaterials*, 13(8):491–496, 1992).

EXAMPLE XI

The ability of PDGF-BB and vitamin D to stimulate periosteal bone formation in neonatal rat femurs and calvaria of 5 week old mice is tested using PDGF, vitamin D or a combination of PDGF and vitamin D. For testing in femurs, the dose range of PDGF used is 2 to 200 ng per day. The dose range for vitamin D used is 20 ng to 2 μg per day. The compounds are injected into the periosteum at the mid-anterior aspect of the left femur in newborn rat pups (2–3 days old) for ten consecutive days. The contralateral femur serves as the vehicle control. The bones are labeled for histomorphometry by an intraperitoneal injection of tetracycline ( 10 mg/kg) on day 5 and calcein intraperitoneal injections (10 mg/kg) on days 17 and 22. Eight rat pups are used for each treatment group. On day 24, the animals are euthanized, and both femurs are removed and processed for undecalcified bone histomorphometry.

Examination of bone formation in calvaria is made by injecting PDGF, vitamin D or a combination of PDGF and vitamin D subcutaneously into the periosteal tissues overlying the sagittal suture. The injections are made once per day for 10 days. The dose range of PDGF used is 2 to 200 ng per day. The dose range for vitamin D used is 20 ng to 2 μg per day. New bone formation is labeled for measurement by intraperitoneal injection of tetracycline on day 1 and intraperitoneal injections with calcein on days 18 and 25. The mice are sacrificed on day 28, and the calvaria is harvested and processed for histological evaluation.

Although the foregoing invention has been described in some detail by way of illustration and example for purposes of clarity of understanding, it will be evident that certain changes and modifications may be practiced within the scope of the appended claims.

What is claimed is:

1. A method for stimulating the in vitro growth of osteoblast cells comprising:

applying to the cells a composition comprising platelet-derived growth factor (PDGF) in combination with vitamin D in an amount sufficient to stimulate osteoblast growth at least 50% as measured by incorporation of $^3$H-thymidine, as compared to cells grown in the presence of PDGF and absence of vitamin D.

2. A method according to claim 1, wherein the composition is essentially free of PDGF A chain.

3. A method according to claim 1, wherein the composition comprises recombinant PDGF-BB.

4. A method according to claim 1, wherein the concentration of PDGF in said composition is from 1 ng/ml to 100 ng/ml.

5. A method according to claim 1, wherein the concentration of PDGF in said composition is from 5 ng/ml to 40 ng/ml.

6. A method according to claim 1, wherein the ratio of PDGF:vitamin D in said composition is from 6:1 to 6:500.

7. A method according to claim 6, wherein the ratio of PDGF:vitamin D in said composition is from 6:10 to 6:100.

8. A method for stimulating bone growth in a patient in need thereof, comprising administering to said patient an effective amount of a composition comprising PDGF and vitamin D, wherein said composition produces at least a 10% increase in bone mass.

9. A method according to claim 8, wherein the vitamin D is 9,10-secocholesta-5,7,10[19]-trien-3-ol or 1α,25-dihydroxycholecaliferol [9,10 1α,25-dihydroxycholecaliferol].

10. A method according to claim 8, wherein the composition is delivered locally to a bone wound or defect.

11. A method according to claim 8, wherein the ratio of PDGF: vitamin D in said composition is from 6:1 to 6:500.

12. A method according to claim 8, wherein the ratio of PDGF:vitamin D in said composition is from 6:10 to 6:100.

13. A method according to claim 8, wherein the composition is essentially free of PDGF A chain.

14. A method according to claim 8, wherein the composition comprises recombinant PDGF-BB.

15. A method for stimulating the in vitro growth of osteoblast cells comprising culturing said cells in the presence of an amount of a composition comprising PDGF and vitamin D sufficient to stimulate osteoblast growth at least 50% as measured by incorporation of $^3$H-thymidine, as compared to cells grown the presence of PDGF and absence of vitamin D, wherein said composition is essentially free of the A-chain of PDGF.

* * * * *